United States Patent [19]

Hempenius et al.

[11] 4,101,883

[45] Jul. 18, 1978

[54] KEYBOARD

[75] Inventors: Klaas Hempenius; Jan Cornelis Van Mourik; Petrus Franciscus Stevens, all of Eindhoven, Netherlands

[73] Assignee: U.S. Philips Corporation, New York, N.Y.

[21] Appl. No.: 789,212

[22] Filed: Apr. 20, 1977

Related U.S. Application Data

[63] Continuation of Ser. No. 590,438, Jun. 26, 1975, abandoned.

[30] Foreign Application Priority Data

Jul. 15, 1974 [NL] Netherlands .......................... 7409515

[51] Int. Cl.² .............................................. G08C 11/00
[52] U.S. Cl. .................................... 340/365 R; 35/17; 128/2.05 R; 340/525; 340/337
[58] Field of Search ................... 340/225, 337, 365 R, 340/365 C; 35/9 C, 17; 128/2 H, 2.05 R

[56] References Cited

U.S. PATENT DOCUMENTS

| 2,094,134 | 9/1937 | Obergfell | 340/225 |
| 2,361,412 | 10/1944 | Paulus et al. | 340/225 |
| 3,056,121 | 9/1962 | Jackson | 340/225 |
| 3,123,067 | 3/1964 | Clark | 128/2.05 R |
| 3,382,588 | 5/1968 | Serrell et al. | 340/365 C |
| 3,766,908 | 10/1973 | Haynes | 128/2.05 R |
| 3,886,539 | 5/1973 | Gould | 340/337 |
| 3,888,491 | 6/1975 | Bernard et al. | 340/337 X |

Primary Examiner—David L. Trafton
Attorney, Agent, or Firm—Frank R. Trifari

[57] ABSTRACT

A keyboard for a physiological measuring system, comprising a group of location indication buttons which are arranged on an image of, for example, the heart at locations which correspond to feasible measuring positions. Furthermore, there are preferably provided a number of selection buttons, each of which can have a location indication button associated therewith. This is made visible by means of signal lamps which are arranged adjacent each location indication button.

2 Claims, 1 Drawing Figure

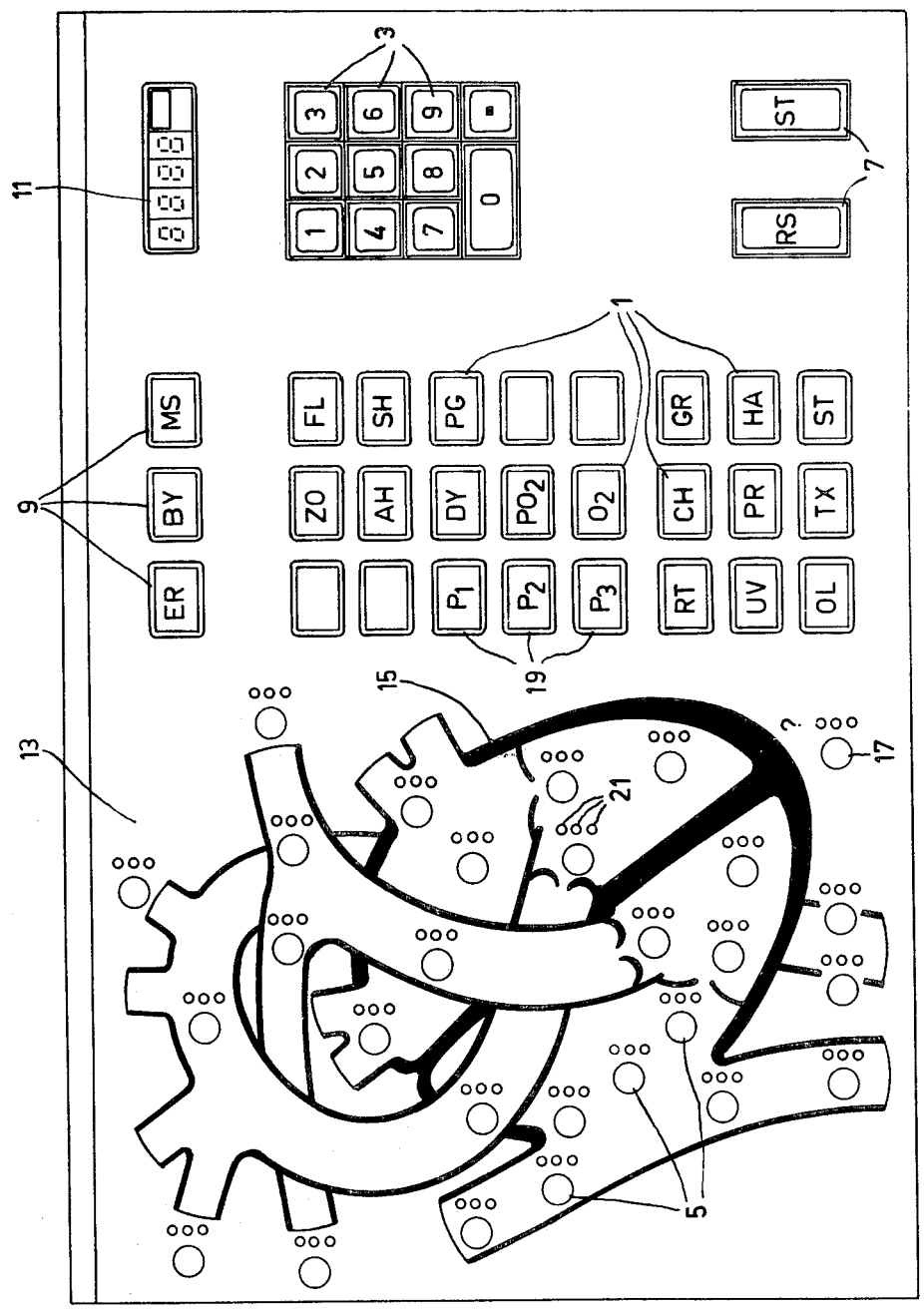

KEYBOARD

This is a continuation, of application Ser. No. 590,438, filed June 26, 1975 now abandoned.

The invention relates to a keyboard for a physiological measuring system provided with a data processing device, comprising a number of groups of buttons for the input of commands and data, including a group of location indication buttons for the input of the position of an examination point in the physiological system (measuring position).

Physiological measuring systems of this kind are often used in combination with a catheter or an other probe which is introduced into the body, for example, for examining kidneys, the stomach, bronchial tubes, blood circulation etc. An example thereof is a catherization system described in "Measuring for Medicine and the life sciences", Vol. 6, No. 1 (May 1971), pages 1 - 6. Keyboard associated with this system comprises a group of buttons for the input of numerical data, a group for the input of functions, and a pressure measuring group comprising location indication buttons. The latter group comprises buttons whereby it is possible to indicate the location where the blood pressure is measured by means of a catheter. These locations are denoted by means of symbols, for example, RA for right atrium, LV for left ventricle, etc.

If a large number of feasible measuring locations is to be taken into account, a large number of such buttons is required, so that the risk of incorrect selection of a button increases and so that this choice requires a comparatively large amount of attention. Moreover, it is difficult to find meaningful and directly understandable symbols for the buttons if a number of different feasible measuring locations in one space of the heart or in a blood vessel are to be indicated.

The invention has for its object to provide a keyboard whereby these problems are eliminated and on which a very large number of location indication buttons can be present, while the desired location indication button can still be found in one glance. To this end, the keyboard according to the invention is characterized in that the group of location indication buttons is provided on a surface on which an image of at least a part of the physiological system is depicted, at least a part of the location indication buttons being situated at locations of the image which correspond to feasible measuring positions. A major advantage thereof is that the operator using the keyboard is fully acquainted with this kind of image.

In many cases a comparatively small number of measuring locations is to be selected from the large number of feasible measuring locations for use in a given examination for example, pressure measurement.

In order to enable this section, a preferred embodiment of the keyboard according to the invention is characterized in that a number of selection buttons is provided, each of which can temporarily have a location indication button associated therewith, while at the area of each location indication button signalling means are provided to indicate the selection button with which the location indication button is associated.

The invention will be described in detail hereinafter with reference to the drawing which shows an embodiment intended for use in a heart catheterization system. The keyboard comprises a group of function buttons 1, a group of digit buttons 3, a group of location indication buttons 5, a number of special buttons 7, a number of indication lamps 9, and a digital indicator 11. The various buttons may, of course, be conventional push-buttons, but also more modern, for example, capacitively or optically operated switching elements. The function buttons 1 serve to give commands to the heart catheterization system (not shown) for which the keyboard is intended. These commands may concern, for example, the measuring of pressures, velocities, oxygen concentrations etc. and also the calculation of given physiological quantities from the measured values. The digit buttons 3 serve for the input of numerical data.

The location indication buttons 5 serve for the input of a measuring position, i.e. for the position occupied by a detector of a catheter introduced into the vascular system of a patient. They are provided on a surface 13 on which a diagrammatic drawing 15 of the heart and the main blood vessels opening into the heart is provided. At any location of the image corresponding to a feasible measuring position, a location indication button 5 is provided. A feasible measuring position is a position in which the operator assumedly would like to perform a measurement in relevant cases. In order to enable measurements to be made at a different location or at a location which is not exactly known, a location indication button 17 is also arranged oustide the image 15. If desired, more of such additional buttons can be provided, and images of other parts of the circulatory system can be depicted on the surface 13. The indication of the location where a detector is situated is simply effected by depressing the relevant location indication button 5, after which a measurement can be performed at this location by depressing the relevant function button 1; for example, a measurement of the oxygen concentration is performed by depressing the function button marked $O_2$.

It often occurs that at a number of locations, for example, blood pressure must be regularly measured. It is then possible to depress the relevant location indication button and function button each time, but it is easier and safer (less risk of errors) if each time only one button need be depressed. To this end, three selection buttons 19, marked $P_1$, $P_2$ and $P_3$, are provided for the function "blood pressure measurement". For example, when selection button $P_1$ and one of the location indication buttons 5 are depressed, the relevant location indication button is assigned to the button $P_1$. The said location indication is then assigned to the next measurement. In order to make it possible to see in one glance which location indication buttons 5 are assigned to which selection buttons 19, signalling means are provided in the form of a row of three signal lamps 21 adjacent each location indication button. If a location indication button is assigned to the selection button $P_1$, the upper lamp 21 adjacent the said location indication button lights up; for selection button $P_2$ the central lamp lights up, while for $P_3$ the lower lamp lights up. The number of selection buttons and the number of signal lamps can be adapted as desired. Instead of signal lamps 21, other signalling means such as luminescing digits can alternatively be used.

What is claimed is:

1. In computerized medical apparatus for diagnosing a physiological system said apparatus having on a keyboard a plurality of location command keys for operator communication to the apparatus of the location in the physiological system of an input element making a physiological measurement, improved means for identifying to the operator the physiological location associated with each of the location command keys, said improvement comprising: a diagramatic image representation of the physiological system on the keyboard background, the image representation including at least that portion of the physiological system at which input physiological measurements might be taken, each of the location command keys being physically located at the position on the image representation corresponding to the location in the physiological system communicated to the apparatus by actuation of that key.

2. Improved medical apparatus as defined in claim 1 wherein the image representation is of the heart of a mammal and adjacent portions of the major blood vessels opening into the heart.

* * * * *